United States Patent [19]

Harrison

[11] Patent Number: 5,646,962
[45] Date of Patent: Jul. 8, 1997

[54] APPARATUS FOR REDUCING ELECTROMAGNETIC RADIATION FROM A DIFFERENTIALLY DRIVEN TRANSMISSION LINE USED FOR HIGH DATA RATE COMMUNICATION IN A COMPUTERIZED TOMOGRAPHY SYSTEM

[75] Inventor: Daniel David Harrison, Delanson, N.Y.

[73] Assignee: General Electric Company, Schenectady, N.Y.

[21] Appl. No.: 349,220

[22] Filed: Dec. 5, 1994

[51] Int. Cl.[6] .................................. H04L 27/20
[52] U.S. Cl. ..................... 375/308; 378/4; 332/103
[58] Field of Search ........................ 375/261, 298, 375/279, 281, 308, 257; 333/12; 332/103, 108; 455/59, 60, 61; 378/4, 21

[56] References Cited

U.S. PATENT DOCUMENTS

| | | | |
|---|---|---|---|
| 4,218,586 | 8/1980 | Parker et al. | 455/61 |
| 4,726,039 | 2/1988 | Piesinger | 375/308 |
| 4,736,170 | 4/1988 | Wu et al. | 375/308 |
| 4,940,954 | 7/1990 | Aubert et al. | 375/298 |
| 5,208,581 | 5/1993 | Collins . | |
| 5,229,871 | 7/1993 | Czarnek et al. . | |
| 5,434,887 | 7/1995 | Osaka | 375/308 |

*Primary Examiner*—Stephen Chin
*Assistant Examiner*—T. Ghebretinsae
*Attorney, Agent, or Firm*—Donald S. Ingraham

[57] ABSTRACT

Apparatus for reducing electromagnetic radiation from a differentially driven transmission line for high data rate communication in a computerized tomography system is provided. The apparatus includes a carrier generator to generate carrier signals having an adjustable phase shift angle between one another. The phase angle differential is selected to avoid formation of leakage signals due to misalignment occurring between the coupler and the transmission line during relative movement therebetween, thereby reducing electromagnetic radiation from the transmission line and the coupler.

26 Claims, 4 Drawing Sheets fig. 1 fig. 2 fig. 3 fig. 4 fig. 5 fig. 6

APPARATUS FOR REDUCING ELECTROMAGNETIC RADIATION FROM A DIFFERENTIALLY DRIVEN TRANSMISSION LINE USED FOR HIGH DATA RATE COMMUNICATION IN A COMPUTERIZED TOMOGRAPHY SYSTEM

BACKGROUND OF THE INVENTION

The field of the present invention is generally related to computerized tomography (CT) and, more particularly, to an apparatus for reducing electromagnetic radiation from a differentially-driven transmission line for providing high data rate communication in a CT system.

CT systems typically employ a rotating frame or gantry to obtain multiple x-ray images, or views, at different rotational angles. Each set of images is referred to in the art as a "slice". A patient or inanimate object is generally positioned in a central opening of the rotating frame on a table which is movable axially, thus enabling respective slices to be obtained at multiple axial positions as well. Each of the slices obtained is then processed in a computer according to predetermined algorithms to produce enhanced images for diagnostic or inspection purposes.

The rotating frame includes an x-ray source, a detector array and electronics necessary to generate image data for each view. A set of stationary electronics is employed for processing raw image data into the enhanced form. Thus, it is necessary to provide for communication of the image data between the rotating frame and a stationary frame of the CT system.

The data rate for communication between the stationary and rotating frames is an important factor because it is desirable to obtain the desired views as fast as possible to reduce patient discomfort and/or to maximize equipment utilization. In current CT systems, a single view typically comprises about 800 detector channels with a 16 bit representation for each individual detector channel output (i.e., 12.8 Kbits per view) and is typically repeated 1,000 times per second, yielding a net data rate requirement of approximately 13 Megabits per second (Mbit/sec) for image data alone. Future CT systems capable of simultaneously constructing multiple image slices by employing four, eight, or sixteen times as many detector channels will increase the data rate requirement to beyond 150 Mbit/sec for image data alone.

Prior CT systems have employed brushes and slip rings for electrically linking the rotating frame to the stationary frame. However, in general, CT systems utilizing brushes and slip rings for communications have generally suffered from significant limitations in the data rates which can be achieved. This is due to the substantial time required to propagate the signals around the circular slip rings. At the desired data rates, the electrical path length around the rings is an appreciable fraction of a bit period, so that electromagnetic waves propagating around the rings in opposite directions may arrive at a reception point at substantially different times in a bit period, causing garbled reception.

U.S. Pat. No. 5,208,581 issued to A. K. Collins, assigned to the assignee of the present invention and herein incorporated by reference, is another type of gantry in which brushes and slip rings are employed for communication. Although the design of Collins provides relatively high speed communication between the stationary and rotating frames, the fact remains that the use of contacting brushes and rings inherently carries certain disadvantages. For example, the mechanical contact between the brushes and rings causes wear which requires such brushes and rings to be periodically replaced in order to maintain reliable communication. Furthermore, the slip-ring design of Collins does not support the higher data rates needed for multiple-slice CT systems.

Other CT systems have employed an optical data link for communication between the stationary and rotating frames. Although an optical data link design avoids typical drawbacks of slip rings and brushes, such optical design requires optics which must be fabricated under tight specifications and which in operation require substantial spatial alignment in order to achieve reliable optical coupling along the relatively long circumference of the rotating frame. This leads to high costs and, thus, it is desirable to provide in a CT system an improved communication link which at a low cost provides reliable high data rate communication between the stationary and rotating frames of the CT system.

It is further desirable to provide a communication link between the stationary frame and the rotating frame which is robust with respect to electromagnetic radiation interference such as is typically produced in a hospital environment by cellular telephones, defibrillating devices, surgical saws and even electrical noise produced by any given CT system. Furthermore, it is also desirable to reduce the level of electromagnetic energy which is radiated from such communication link in order to comply with governmental regulations such as regulations imposed by the Federal Communications Commission and/or foreign governments. As described in U.S. Pat. No. 5,530,424, a transmission line and a coupler or probe provide means for implementing such high data rate communication link. As further described in U.S. Pat. No. 5,530,422, a differentially driven transmission line and coupler allow for substantially avoiding electromagnetic radiation around the coupler. Although the differential techniques described in 5,530,422 advantageously reduce some electromagnetic radiation around the coupler as the coupler moves relative to the transmission line, it is desirable to reduce leakage signals due to mechanical misalignment between the transmission line and the coupler during relative movement between the transmission line and the coupler. Each of the above-identified U.S. patents is assigned to the assignee of the present invention and is herein incorporated by reference.

SUMMARY OF THE INVENTION

Generally speaking, the present invention fulfills the foregoing needs by providing an apparatus for reducing electromagnetic radiation from a differentially driven transmission line for providing high data rate communication in a computerized tomography system. The apparatus comprises a carrier generator to generate first and second carrier signals having an adjustable phase shift angle between one another in response to an externally-derived control signal applied thereto; and modulating means, such as balanced modulators, respectively coupled to the carrier generator for receiving the first and second carrier signals and for receiving an externally-derived data signal, such as image data, to produce first and second modulated output signals having a variable phase angle differential between one another in accordance with the phase shift between said first and second carrier signals. The phase angle differential is selected to substantially avoid formation of leakage signals due to misalignment occurring between the coupler and the transmission line during relative movement therebetween, thereby reducing electromagnetic radiation from the transmission line and the coupler.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like numbers represent like parts throughout the drawings, and in which:

DETAILED DESCRIPTION OF THE INVENTION

Figure 1:
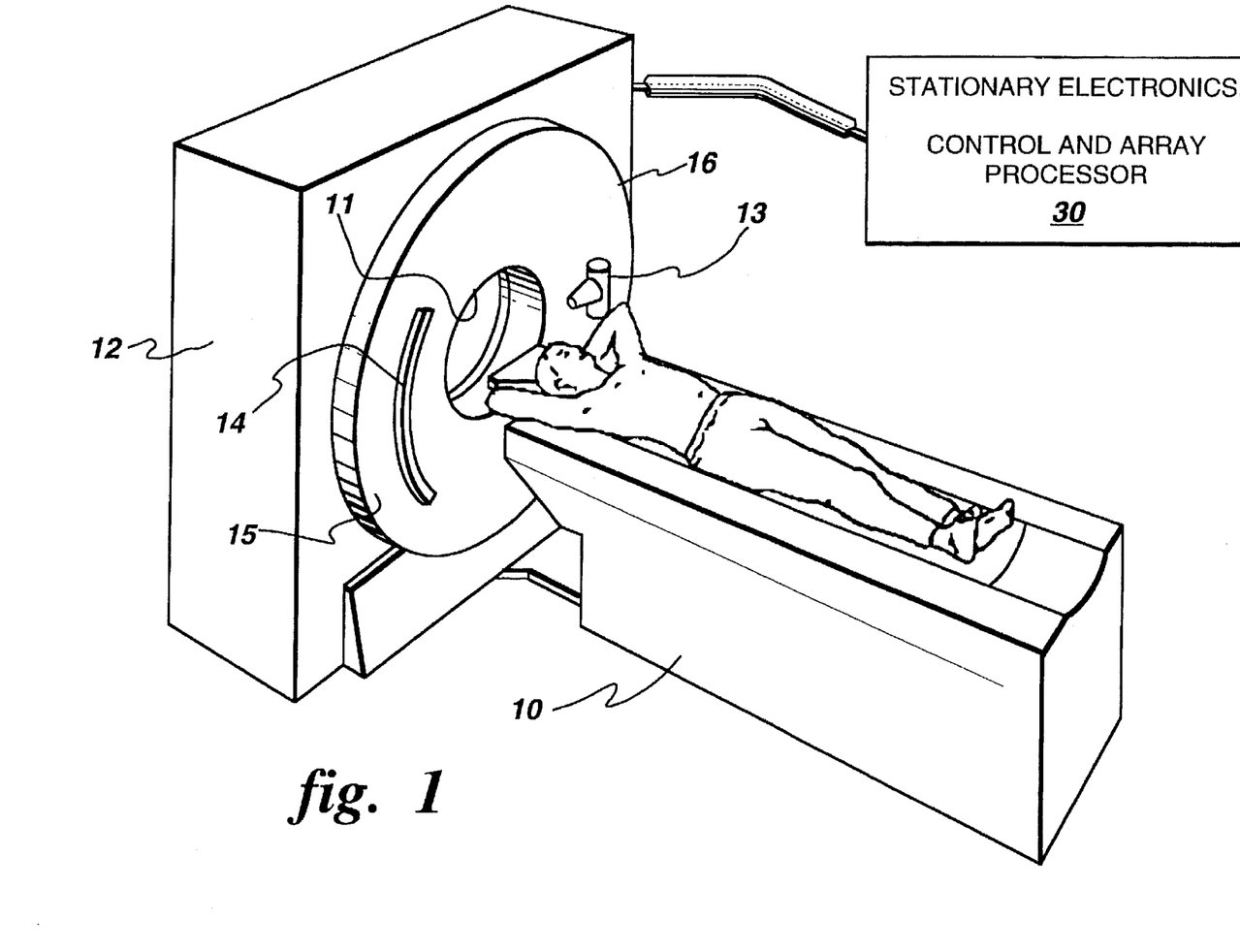
FIG. 1 is a perspective view of a CT system which employs the present invention.

As shown in FIG. 1, a CT system used to produce images of at least a region of interest of the human anatomy has a patient table 10 which can be positioned within the aperture 11 of a generally annular rotating frame or gantry 15 having a predetermined circumference, e.g., outer circumference 16. A stationary frame 12 is conveniently employed to support rotating frame 15. A source of imaging energy 13 which preferably produces highly collimated x-rays is mounted on the rotating frame to one side of its aperture 11, and a detector array 14 is mounted to the other side of the aperture. The rotating frame, together with x-ray source 13 and detector array 14, is revolved about the aperture during a scan of the patient to obtain x-ray attenuation measurements from many different angles through a range of at least 180° of revolution. Detector array 14 may comprise multiple rows each having about 800 detector channels along its length. The individual outputs of each channel in detector array 14 is connected to a data acquisition system, DAS (not shown). When sampled, each channel output is converted by the DAS to, for example, a 16 bit digital value representing X-ray intensity.

The rotating frame further includes additional onboard electronics (not shown) which rotates along with rotating frame 15. The onboard electronics is essentially a slave to stationary electronics systems 30 which is located off rotating frame 15. Stationary electronics systems 30 is a computer-based system for issuing commands to the onboard electronics on rotating frame 15 and for receiving the resulting image data, via suitable electrical leads from stationary frame 12, to perform processing of the received image data.

The present invention is directed to apparatus for reducing electromagnetic radiation from a differentially driven transmission line for providing high data rate communication in a computerized tomography system. The high data rate communication is noncontactively provided between the rotating frame and the stationary frame through radio coupling between the differentially driven transmission line and a differential coupler. This advantageously avoids the use of slip rings and brushes and allows for continuous rotation of rotating frame 15. As discussed above, multiple-slice CT systems require high data rate communication which is reliable, and which is in compliance with electromagnetic emission regulations. The present invention advantageously allows for such high data rate communication, (e.g., exceeding 150 Mbits/sec.) while reducing radiation or leakage of electromagnetic energy, such as can be produced due to mechanical misalignment between the transmission line and the coupler, i.e., the relative misalignment therebetween. This high data rate communication is conveniently implemented without the use of brushes and slip rings or without the use of costly optical devices. Further, the present invention allows for reliable and cost effective high data rate communication notwithstanding the relatively long circumference (approximately 13 ft) of the rotating frame.

In the discussion which follows, it is assumed that all of the communication between rotating frame 15 and stationary frame 12 has been serialized, i.e., converted from parallel to serial data for transmission and vice versa on reception, employing well known multiplexing techniques. This is done so that only a single bit stream need be transmitted, although it should be apparent to those skilled in the art that multiple parallel paths according to the present invention could be employed. In each case, multilevel or multiphase encoding techniques can be employed to further increase the maximum data rate available.

Figure 2:
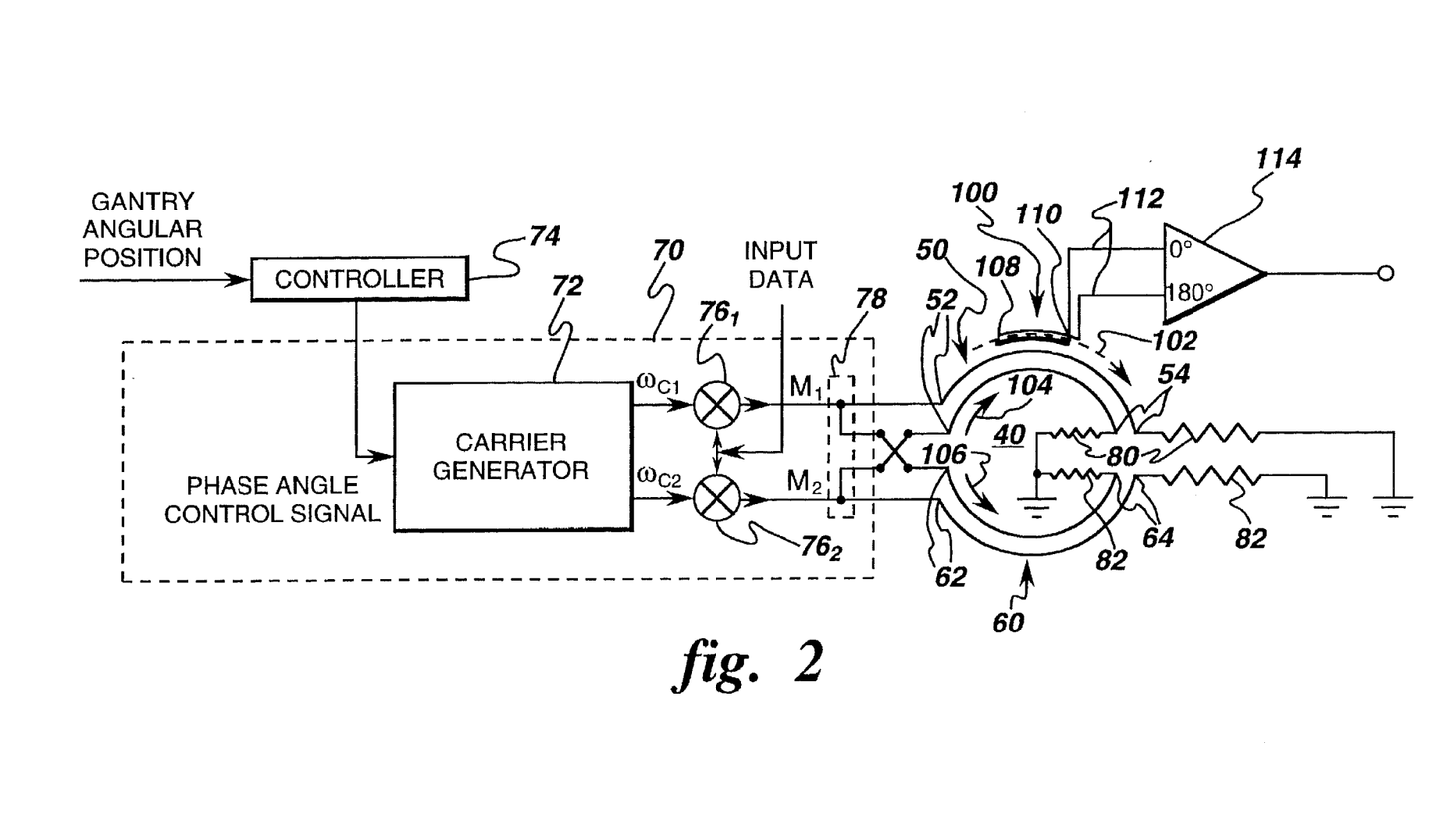
FIG. 2 is a simplified schematic representation of an apparatus for reducing electromagnetic radiation in accordance with the present invention including a differential transmission line driven by the apparatus, and a differential coupler.
Figure 3:
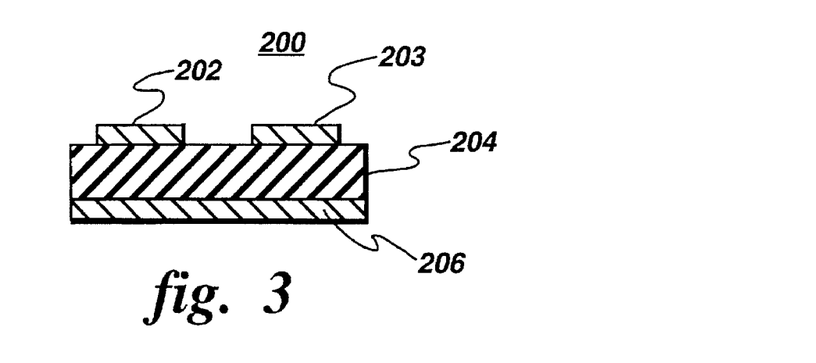
FIG. 3 is a cross section of a microstrip which can be utilized for the differentially driven transmission line and/or differential coupler shown in FIG. 2.

As shown in FIG. 2, a differentially driven transmission line 40 is attached to rotating frame 15 (FIG. 1) and is positioned substantially around the rotating frame, for example, around the circumference of the rotating frame. Similarly, the transmission line can be conveniently affixed to the annulus of the rotating frame, i.e., the surface bounded by the concentric circles in the rotating frame; for example, the concentric circle which defines aperture 11 and the larger concentric circle which has circumference 16. Further, it will be appreciated that the transmission line need not be limited to circular geometric arrangements since geometric arrangements other than circular can equally benefit from the present invention. By way of example, transmission line 40 comprises respective individual segments 50 and 60 each having a respective first end 52 and 62, and a respective second end 54 and 64. In FIG. 2, each respective individual segment is represented by twin lines since, as shown in FIG. 3 by way of example and not of limitation, each of the individual segments comprises electromagnetically coupled microstrip transmission lines having respective signal conductors for carrying respective signals being sufficiently out-of-phase with respect to one another to substantially cancel leakage signals due to misalignment between respective transmission line segments and the coupler, that is, each segment may comprise coupled microstrip transmission lines differentially and adaptably driven, as will be explained shortly hereafter, to achieve substantial cancellation of any such leakage signals. Preferably, each individual segment 50 and 60 has a respective electrical length chosen so that a modulated signal applied at each respective first end 52 and 62 has a predetermined time-delay upon arrival at each respective second end 54 and 64. It will be appreciated that if the respective electrical lengths for segments 50 and 60 are substantially similar to one another, the above-described segment arrangement results in the modulated signal arriving at each respective second end with a substantially similar time delay relative to one another.

FIG. 2 further shows an apparatus 70 that advantageously and in accordance with the present invention allows for reducing electromagnetic radiation from the differentially driven transmission line. By way of example, apparatus 70 can be conveniently mounted on rotating frame 15 as part of the onboard electronics. Apparatus 70 comprises a carrier generator 72 designed to generate first and second carrier signals $\omega_{c1}$ and $\omega_{c2}$ having an adjustable or variable phase shift angle between one another. Preferably, the phase shift angle is readily adjusted or varied in response to an externally-derived control signal, such as a phase angle control signal provided by a suitable controller 74. It will be appreciated that an adjustable phase shift angle is desirable between the first and second carrier signals $\omega_{c1}$ and $\omega_{c2}$ in order to electrically compensate for misalignment encountered during relative movement between the transmission line and the probe. As suggested above, it is desirable to compensate for such misalignment since the operation of the communication link between the transmission line and the probe can be degraded due to leakage signals which can form due to coupler and/or transmission line alignment errors. It will be apparent to those skilled in the art that, if zero mechanical misalignment were present at each gantry angular position between the transmission line and the coupler, then the desired phase shift angle between the first and second carrier signals would be, for example, substantially 180° at each gantry angular position and no phase angle deviation or shift from 180° would be required. However, in actual practice it is typical to encounter some misalignment between the transmission line and the coupler, and thus the phase shift angle between the first and second carriers is preferably adaptably adjusted or varied by angles other than 180° in order to suitably compensate for any such misalignment. It can be shown that such misalignment is substantially repeatable as a function of gantry angular position, that is, the relative misalignment between the transmission line and the coupler can be readily characterized or measured as a function of gantry angular position. For example, misalignment measurements can be prerecorded in controller 74, or, alternatively, the controller could be coupled to a sensor (not shown) which conveniently measures in real time the misalignment between the transmission line and the coupler as a function of gantry angular position. In each case, controller 74, based upon suitably obtained misalignment measurements, provides a control signal for adaptably varying the phase shift angle between the first and second carrier signals in order to electrically compensate for misalignment between the transmission line and the coupler, and thus reduce electromagnetic radiation or leakage from the transmission line and the coupler. Modulating means, such as balanced modulators $76_1$ and $76_2$, are respectively coupled to carrier generator 72 for receiving first and second carrier signals $\omega_{c1}$ and $\omega_{c2}$ and for receiving input data, such as image data and the like, to produce first and second modulated output signals $M_1$ and $M_2$ having a variable phase angle differential between one another in accordance with the phase shift between the first and second carrier signals. For example, if the phase shift angle between carrier signals $\omega_{c1}$ and $\omega_{c2}$ is $(180°+\Delta°)$, then first and second modulated ouput signals $M_1$ and $M_2$ would similarly have the same phase angle differential between one another. As suggested above, the phase angle differential is adaptably selected to substantially avoid formation of leakage signals due to misalignment occurring between the coupler and the transmission line during relative movement therebetween. Thus, in operation, apparatus 70 conveniently allows for reducing electromagnetic radiation around the coupler, as the coupler moves relative to the transmission line. The respective first and second carrier signals can be modulated in modulator $76_1$ and $76_2$ by employing any of a number of readily available modulation techniques, such as frequency-shift keying and the like. See chapter 6 of textbook entitled "Principles of Communication Systems" by H. Taub and D. L. Schilling, published by the McGraw-Hill Book Company and herein incorporated by reference for additional details of various pulse-code modulation techniques that could be readily employed in modulators $76_1$ and $76_2$. The first and second modulated signals supplied by modulator $76_1$ and $76_2$ can be readily split or divided by a suitable dividing network 78 into one or more sets of modulated differential signals. For example, as shown in FIG. 2, the first and second modulated signals are split into two respective sets of modulated differential signals so that one differential signal set is supplied to one of the respective transmission line segments while the other differential signal set is supplied to the other one of the transmission line segments. Further, any desired signal conditioning, such as amplification and impedance matching, can be readily provided in a signal conditioning circuit (not shown) which can include matching resistors having a predetermined resistance value selected to match the impedance characteristics of the respective transmission line segments. As shown in FIG. 2, each modulated differential signal set from dividing network 78 is respectively connected to each respective first end 52 and 62. Similarly, each respective second end 54 and 64 is respectively connected to termination resistors 80 and 82 having a predetermined resistance value chosen to minimize reflection of energy in individual transmission line segments 50 and 60. Other arrangements may be employed which, although having some difference in time delay between individual segments, such time-delay difference can be tolerated depending on the specific application. For example, one of the differential signal sets could be respectively connected to each respective second end 64 in lieu of each first end 62, and termination resistors 82 could be respectively connected to each first end 62 in lieu of each second end 64. In this case, although a predetermined time delay would exist between the individual segments, such time delay difference could be acceptable in certain applications.

Individual segments 50 and 60 are preferably arranged so that respective first ends of any two consecutive segments are substantially adjacent to one another and respective second ends of any two consecutive segments are substantially adjacent to one another. The gap size between any two consecutive segments should be small relative to carrier wavelength. For example, about ⅛ in. for a 750 MHz carrier. This arrangement conveniently allows for avoiding time-delay discontinuities between any of the respective individual segments encircling the rotating frame. This allows for effective coupling operation between the transmission line and the coupler at all rotation angles. As shown in FIG. 2, each of the two individual segments 50 and 60 can be designed to subtend a respective angle of about 180° around the circumference of the rotating frame. In general, it will be appreciated that a number of N individual segments each respectively subtending an angle of about 360°/N around the circumference of the rotating frame wherein N is a predetermined even number will be equally effective in alternative embodiments of the present invention since the modulated differential signal (i.e., the net result of the respective modulated signals being adaptively out-of-phase with respect to one another) in each case is available for reception anywhere along the circumference of the rotating frame including any gaps between any of the N individual segments. As suggested above, there may be applications which can tolerate a predetermined time delay difference between the individual segments. In this case, the N number of individual segments need not be limited to an even number since a predetermined odd number of individual segments, including a single segment, could be effectively utilized for applications which tolerate such predetermined time delay difference. The foregoing construction for the individual segments assumes that each segment is made up of a material having a substantially similar dielectric constant. However, it will be apparent that segment materials having predetermined different dielectric constants can also be conveniently employed. In this case, the angle subtended by each respective individual segment need not be identical to each other.

FIG. 2, further shows a differential coupler 100 attached to stationary frame 12 (FIG. 1) and being positioned sufficiently near the differentially driven transmission line for establishing radio coupling therebetween in order to receive the modulated differential signal being applied to the respective individual segments. As used herein the expression "radio coupling" refers to noncontactive transfer of energy by electromagnetic radiation at radio frequencies.

It will be appreciated that coupler 100 has a predetermined length dimension along a coupler axis 102 which, for example, can be substantially parallel relative to individual segments 50 and 60. The coupler length dimension is conveniently chosen to be sufficiently short to substantially avoid frequency-dependent directional coupling effects, and to be sufficiently long to avoid substantial signal reduction in coupler 100 whenever the coupler passes about any gap between respective ones of the individual segments. As indicated by arrows 104 and 106, the modulated differential signal applied to respective segments 50 and 60 propagates in opposite directions and thus to avoid blind spots near any of the gaps, coupler 100 preferably has a first end 110 directly connected to output port means 112, such as a coaxial line pair or other suitably shielded electrical conductor pair, and has a second end 108 which is substantially free of any termination impedance, i.e., termination resistors. In this manner, the modulated differential signal received by coupler 100 passes to coaxial line pair 112 independently of the propagation direction of the received modulated differential signal, i.e., independently of the propagation direction of the respective electromagnetic waves traveling in individual segments 50 and 60. For instance, waves arriving at second end 108 readily propagate toward the first end and from there to coaxial line pair 112, whereas waves arriving at first end 110 are eventually reflected back from the resistively unterminated second end 108 toward the first end and from there to coaxial line pair 112. In each case, differential coupler 100 advantageously allows for noncontactively extracting the respective adaptively out-of-phase signals which constitute the modulated differential signal in the transmission line along the full circumference of the rotating frame. An amplifier 114 can readily provide a predetermined amplification to the respective adaptively out-of-phase signals being supplied by differential coupler 100. As will be appreciated by those skilled in the art, the length dimension of the coupler can vary depending on the specific value of the carrier frequency being utilized for the modulated signal. By way of example and not of limitation, the coupler length dimension can be chosen in the range of $\lambda/4$ to $\lambda/8$ wherein $\lambda$ represents the wavelength of the carrier in the transmission line material. Other configurations for the coupler will be readily apparent to those skilled in the art. For example, a relatively short (e.g., about $\lambda/16$) center-tapped coupler can alternatively be employed in lieu of a coupler having a resistively unterminated end.

FIG. 3 illustrates a cross section of a substantially planar transmission line which can be effectively used both for the differentially driven transmission line segments and for the differential coupler. For example, FIG. 3 shows a microstrip 200 wherein substantially parallel first and second signal conductors 202 and 203 and a ground plane 206 are separated from one another by a suitable dielectric material 204. It will be appreciated that such substantially planar transmission line can be readily fabricated employing well known printed circuit techniques which allow for substantial savings in cost as compared to an optical data link. For additional details such as mode characteristics of the exemplary planar transmission line shown in FIG. 3 and other parallel line devices, see pp. 199–208 of textbook entitled "Microwave Planar Passive Circuits And Filters" by J. Helszajn, published by John Wiley & Sons. Similarly, a stripline transmission line wherein the first and second signal conductors are "sandwiched" in a respective dielectric material between two ground planes can be alternatively employed both for the transmission line segments and for the coupler. A basic construction for a stripline transmission line is shown in FIG. 3b of the above incorporated by reference U.S. Pat. No. 5,530,422. Furthermore, the coupler need not consist of a microstrip or a stripline transmission line. A suitable conductor, such as a short piece of twin wires, aligned substantially parallel to the driven transmission line, will also work effectively.

Figure 4:
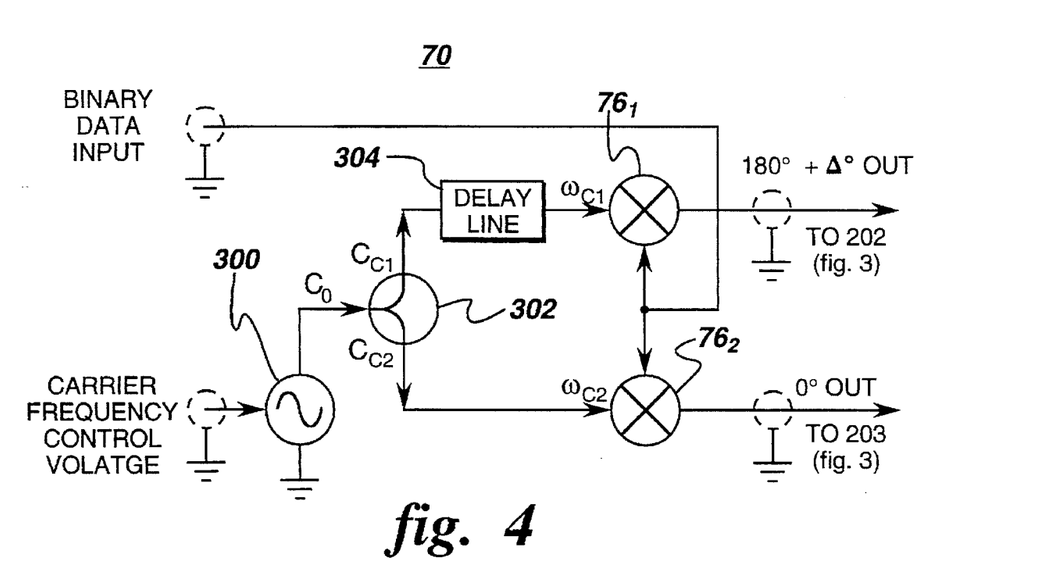
FIG. 4 shows a schematic that provides additional details for one exemplary embodiment for the apparatus shown in FIG. 2.

FIG. 4 shows a schematic of one exemplary embodiment for apparatus 70 in accordance with the present invention. As shown in FIG. 4, an oscillator 300, such as a voltage-controlled oscillator, generates a single carrier signal $C_O$ having a variable frequency in response, for example, to the voltage level of the control signal supplied by controller 74 (FIG. 2). A splitter 302 is electrically coupled to oscillator 300 for splitting or dividing the single carrier signal received from oscillator 300 into two substantially identical carrier-constituent signals $C_{c1}$ and $C_{c2}$. A delay line 304, such as coaxial line is electrically coupled to splitter 302 to receive one of the two carrier-constituent signals. Alternatively, delay line 304 may comprise a substantially planar transmission line such as the microstrip or stripline transmission lines discussed in the context of FIG. 3, except that in this case the transmission line would have a single signal conductor in lieu of the first and second signal conductors shown in FIG. 3. In each case, delay line 304 has a predetermined length L that is sufficiently long in terms of cycles of carrier frequency to produce an output signal having a phase angle delay which varies in accordance with the frequency of the single carrier signal generated by oscillator 300. It can be shown that $$L \propto \frac{\Delta \phi}{\Delta f}, \quad \text{Eq. 1}$$

where $\Delta \phi$ represents a small phase angle delay and $\Delta f$ represents a small change in frequency.

Eq. 1 can be rearranged as follows $$\Delta f \propto L \Delta \phi \quad \text{Eq. 2,}$$

which shows that a small change in frequency can result in a delay line output signal having a substantial phase-angle delay with respect to the undelayed carrier constituent signal. It will be appreciated that in this embodiment, the delay line output signal and the other carrier-constituent signal (i.e., the undelayed carrier constituent signal), respectively, constitute the first and second carrier signals $\omega_{c1}$ and $\omega_{c2}$. Thus, the phase-angle delay imparted by delay line 304 advantageously results in the first and second carrier signals having a phase angle differential being sufficient for electrically compensating any misalignment between the coupler and the transmission line. The first and second carrier signals $\omega_{c1}$ and $\omega_{c2}$ are in turn respectively supplied to modulators $76_1$ and $76_2$ to be multiplied or mixed with input data, such as image data, which can be conveniently encoded using a suitable binary representation. For example, the binary data can be encoded using two respective voltage levels such as 0 and +V volt levels. Alternatively, the two voltage levels could be selected at $-V$ and +V volt levels, respectively.

Figure 5:
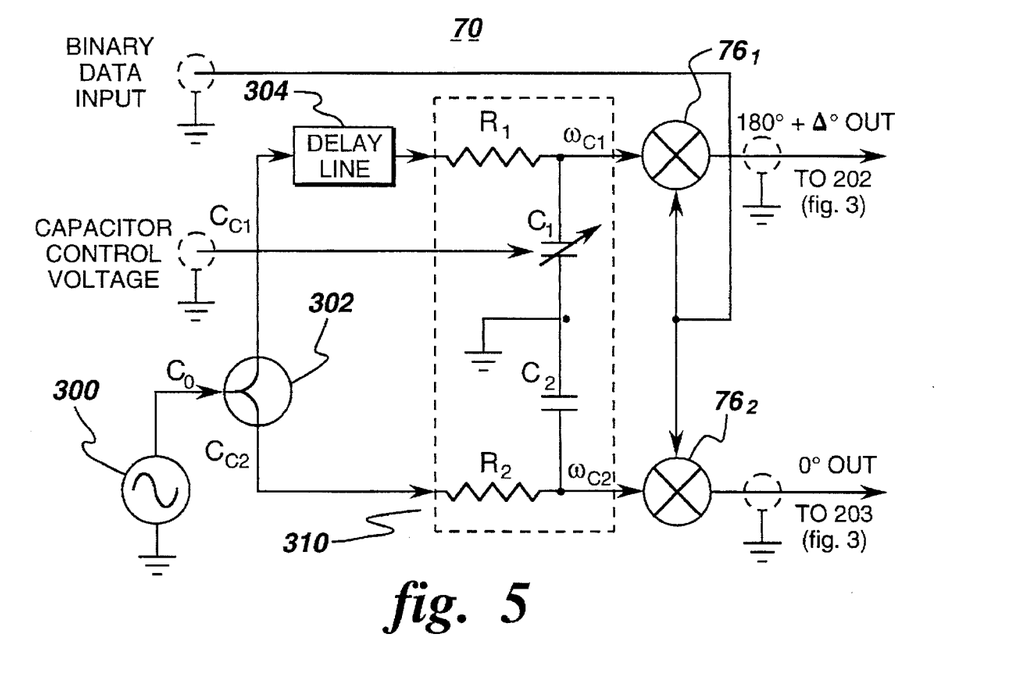
FIG. 5 shows a schematic that provides additional details of another exemplary embodiment for the apparatus shown in FIG. 2.

FIG. 5 shows an alternative exemplary embodiment for apparatus 70. As shown in FIG. 5, in lieu of varying the frequency of the single carrier signal $C_0$ supplied by oscillator 300 to splitter 302, in this embodiment the single carrier signal $C_0$ being supplied by oscillator 300 has a generally fixed frequency, i.e., single carrier signal $C_0$ has a frequency having a predetermined fixed value. A phase shifting circuit 310 is coupled to receive via resistor $R_1$ the output signal from delay line 304. Phase shifting circuit 310 is also coupled to receive via resistor $R_2$ the other constituent carrier signal (i.e., the undelayed constituent carrier signal) which is directly supplied by splitter 302. Phase shifting circuit 310 allows for producing, in response to the externally-derived control signal, first and second output signals which respectively constitute the first and second carrier signals $\omega_{c1}$ and $\omega_{c2}$. As shown in FIG. 5, phase-shifting circuit 310 comprises a resistance-capacitance network having at least one variable capacitor $C_1$, such as a varactor diode and the like. Preferably, the capacitance value of capacitor $C_2$ is chosen to match the capacitance value of $C_1$ at its mid-range value so that any desired differential phase angle value, either above or below 180°, is achievable between the respective outputs of phase-shifting circuit 310. It will be appreciated that, in this embodiment, delay line 304 provides a delay line output signal having a generally fixed phase delay with respect to the undelayed constituent carrier signal. For example, the fixed phase delay provided by the delay line with respect to the undelayed constituent carrier signal can be 180°. It will be understood by those skilled in the art that other schemes for electronically varying the phase angle differential between the two modulator outputs will be equally effective. For example, delay line 304 could be readily eliminated if splitter 302 were modified for providing substantially out-of-phase output signals in lieu of the substantially identical carrier-constituent signals $C_{c1}$ and $C_{c2}$.

Figure 6:
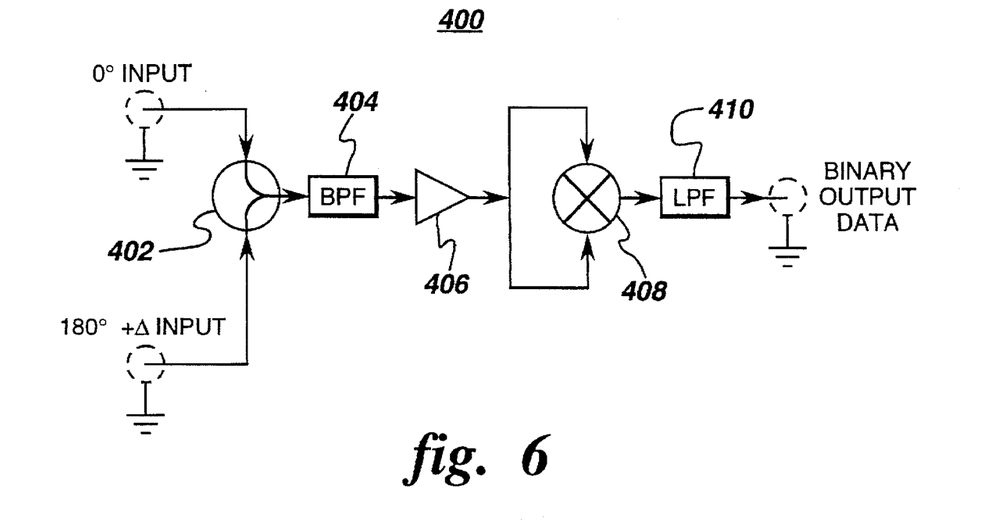
FIG. 6 shows a schematic of one exemplary receiver which can be conveniently used for receiving signals transmitted from an apparatus in accordance with the present invention.

FIG. 6 shows a simplified block diagram of an exemplary receiver 400, such as a differential pulse-amplitude (DPAM) modulation receiver that can be conveniently employed for receiving the respective modulated signals in the differentially driven transmission line. If desired, full use of the differential signals can be achieved by using a 180° hybrid power combiner 402, i.e., power combiner 402 combines the substantially out-of-phase modulated signals into a single combined output signal. A bandpass filter 404 is centered at the predetermined carrier frequency, and protects from outside interference the combined output signal from power combiner 402. Amplifier 406 provides any desired signal gain and mixer 408 demodulates the combined signal using any demodulation technique suitable for the specific modulation technique employed in apparatus 70 (FIG. 2). A low-pass filter 410 removes or filters any out-of-band carrier-frequency component generated by mixer 408. It will be appreciated that many other techniques can be readily employed for demodulating the modulated differential signals provided by the transmission line. For example, even an uncomplicated half-wave or full-wave rectifier and a suitable low-pass filter could provide the desired signal demodulation if desired. The differential receiver shown in FIG. 6, can provide a 3 dB signal level increase over a single-ended receiver and can provide extra protection against common-mode outside interference. However, sensitivity to outside interference is already substantially low because the coupler output ports are shielded by coaxial conductors and by the microstrip ground plane that is part of the coupler. Thus, use of a differential receiver is in general not required, unless further cancellation of common-mode outside interference is desired. That is, the modulated signal from just one of the input lines is sufficient in a single-ended receiver since substantial electromagnetic radiation cancellation occurs if both input lines are properly terminated and shielded. For instance, a single-ended receiver would use only one of the input lines shown in FIG. 6 and would not use power combiner 402.

Although various specific constructions have been given for the present invention, it is to be understood that these are for illustrative purposes only. Various modifications and adaptations will be readily apparent to those skilled in the art without departing from the substance or scope of the invention. For example, although the transmission line segments have been described as rotating along with rotating frame or gantry 15 (FIG. 1) and the coupler has been described as attached to stationary frame 12 (FIG. 1), it is equally possible to instead have the transmission line segments stationary and the coupler mounted on the rotating frame, i.e., stationary and rotating mechanical mounting for the coupler and transmission line segments can be readily interchanged with equally effective results. Accordingly, it is intended that the invention be limited only by the spirit and scope of the claims appended hereto.

What is claimed is:

1. Apparatus for reducing electromagnetic leakage from a differentially driven transmission line for providing high data rate communication in a computerized tomography system comprising:

a carrier generator to generate first and second carrier signals having an adjustable phase angle difference between said respective carrier signals in response to a control signal applied thereto;

a first and a second modulator respectively coupled to said carrier generator for receiving said first and second carrier signals and for receiving an externally-derived data signal to produce a first and a second modulated output signal having said adjustable phase angle difference therebetween;

a transmission line comprising a first and a second signal conductor coupled respectively to said first and said second modulator to receive said first and said second modulated output signals, said transmission line adapted to transmit electromagnetic radiation in correspondence with said first and said second modulated output signals;

a coupler for receiving said electromagnetic radiation transmitted by said transmission line; and a controller coupled to said carrier generator for generating said control signal so as to control said adjustable phase angle difference between said first carrier signal and said second carrier signal, wherein said phase angle difference is selected to minimize electromagnetic leakage between said coupler and said transmission line.

2. The apparatus of claim 1 wherein said carrier generator comprises:
   an oscillator for generating a single carrier signal having a variable frequency in response to said externally derived control signal;
   splitter means for splitting the single carrier signal into two substantially identical carrier-constituent signals; and
   a delay line coupled to said splitter means to receive one of the two carrier-constituent signals, said delay line having a predetermined length sufficient to produce an output signal having a variable phase angle delay in accordance with the frequency of the single carrier signal generated by said oscillator, the delay line output signal and the other carrier-constituent signal, respectively, constituting said first and second carrier signals.

3. The apparatus of claim 2 wherein said first and said second modulators are balanced with respect to one another so that modulation imparted to said first carrier signal and said second carrier signal is the same.

4. The apparatus of claim 3 wherein said delay line comprises a coaxial line.

5. The apparatus of claim 3 wherein said delay line comprises a substantially planar transmission line selected from the group consisting of microstrip and stripline transmission lines.

6. The apparatus of claim 1 wherein said carrier generator comprises:
   an oscillator to generate a single carrier signal;
   a splitter for splitting the single carrier signal into two substantially identical carrier constituent signals;
   a delay line coupled to said splitter to receive one of the two carrier constituent signals, said delay line having a predetermined length sufficient to produce an output signal having a predetermined phase angle delay; and
   a phase-shifting circuit coupled to said delay line to receive the output signal from said delay line and coupled to said splitter to receive the other of the constituent carrier signals to produce, in response to said externally-derived control signal, first and second output signals, respectively, constituting said first and second carrier signals.

7. The apparatus of claim 6 wherein said first and said second modulators are balanced with respect to one another so that modulation imparted to said first carrier signal and said second carrier signal is the same.

8. The apparatus of claim 7 wherein said delay line comprises a coaxial line.

9. The apparatus of claim 7 wherein said delay line comprises a substantially planar transmission line selected from the group consisting of microstrip and stripline transmission lines.

10. The apparatus of claim 7 wherein said phase-shifting circuit comprises a resistance-capacitance network having at least one variable capacitor.

11. The apparatus of claim 1 wherein said carrier generator comprises:
    an oscillator to generate a single carrier signal;
    a splitter to split the single carrier signal into two carrier-constituent signals being substantially out-of-phase with respect to one another; and
    a phase-shifting circuit coupled to said splitter to receive the two carrier-constituent carrier signals to produce, in response to said externally-derived control signal, first and second output signals, respectively, constituting said first and second carrier signals.

12. The apparatus of claim 11 wherein said first and said second modulators are balanced with respect to one another so that modulation imparted to said first carrier signal and said second carrier signal is the same.

13. The apparatus of claim 12 wherein said phase-shifting circuit comprises a resistance-capacitance network having at least one variable capacitor.

14. A computerized tomography system comprising:
    a carrier generator to generate first and second carrier signals having an adjustable phase angle between one another in response to control signal applied thereto;
    a first and a second modulator respectively coupled to said carrier generator for receiving said first and said second carrier signals, each of said modulators being further adapted for receiving an externally-derived data signal to produce first and second modulated signals having said adjustable phase angle difference between one another;
    a transmission line having a first and a second signal conductor coupled respectively to said first and second modulators to respectively receive said first and said second modulated signals; and
    a coupler disposed in a spatial relationship with said first and said second signal conductors so as to establish electromagnetic radiation coupling therebetween said coupler being movable so as to be disposed in each of a plurality of relative positions with respect to said transmission line; and
    a controller coupled to said carrier generator for generating said control signal so as to control said adjustable phase angle difference between said first carrier signal and said second carrier signal to minimize electromagnetic leakage for each of said plurality of relative positions between said transmission line and said coupler.

15. The computerized tomography system of claim 14 wherein said carrier generator comprises:
    an oscillator for generating a single carrier signal having a variable frequency in response to said externally derived control signal;
    splitter means for splitting the single carrier signal into two substantially identical carrier-constituent signals; and
    a delay line coupled to said splitter means to receive one of the two carrier-constituent signals, said delay line having a predetermined length sufficient to produce an output signal having a variable phase angle delay in accordance with the frequency of the single carrier signal generated by said oscillator, the delay line output signal and the other carrier-constituent signal, respectively, constituting said first and second carrier signals.

16. The computerized tomography system of claim 15 wherein said first and said second modulators are balanced with respect to one another so that modulation imparted to said first carrier signal and said second carrier signal is the same.

17. The computerized tomography system of claim 16 wherein said delay line comprises a coaxial line.

18. The computerized tomography system of claim 16 wherein said delay line comprises a substantially planar transmission line selected from the group consisting of microstrip and stripline transmission lines.

19. The computerized tomography system of claim 14 wherein said carrier generator comprises:

an oscillator to generate a single carrier signal;

a splitter for splitting the single carrier signal into two substantially identical carrier constituent signals;

a delay line coupled to said splitter to receive one of the two carrier constituent signals, said delay line having a predetermined length sufficient to produce an output signal having a predetermined phase angle delay; and a phase-shifting circuit coupled to said delay line to receive the output signal from said delay line and coupled to said splitter to receive the other of the constituent carrier signals to produce, in response to said externally-derived control signal, first and second output signals, respectively, comprising said first and second carrier signals.

20. The computerized tomography system of claim 19 wherein said first and said second modulators are balanced with respect to one another so that modulation imparted to said first carrier signal and said second carrier signal is the same.

21. The computerized tomography system of claim 20 wherein said delay line comprises a coaxial line.

22. The computerized tomography system of claim 20 wherein said delay line comprises a substantially planar transmission line selected from the group consisting of microstrip and stripline transmission lines.

23. The computerized tomography system of claim 20 wherein said phase-shifting circuit comprises a resistance-capacitance network having at least one variable capacitor.

24. The computerized tomography system of claim 14 wherein said carrier generator comprises:

an oscillator to generate a single carrier signal;

a splitter to split the single carrier signal into two carrier-constituent signals being substantially out-of-phase with respect to one another; and a phase-shifting circuit coupled to said splitter to receive the two carrier-constituent carrier signals to produce, in response to said externally-derived control signal, first and second output signals, respectively, constituting said first and second carrier signals.

25. The computerized tomography system of claim 24 wherein said first and said second modulators are balanced with respect to one another so that modulation imparted to said first carrier signal and said second carrier signal is the same.

26. The computerized tomography system of claim 25 wherein said phase-shifting circuit comprises a resistance-capacitance network having at least one variable capacitor.

* * * * *